US012639814B2

(12) United States Patent
Zhao et al.

(10) Patent No.: US 12,639,814 B2
(45) Date of Patent: May 26, 2026

(54) MEDICAL RECORD-GUIDED COMPUTER-AIDED DETECTION

(71) Applicant: Siemens Healthineers AG, Forchheim (DE)

(72) Inventors: Yiyuan Zhao, Chesterbrook, PA (US); Gerardo Hermosillo Valadez, West Chester, PA (US)

(73) Assignee: Siemens Healthineers AG, Forchheim (DE)

( * ) Notice: Subject to any disclaimer, the term of this patent is extended or adjusted under 35 U.S.C. 154(b) by 293 days.

(21) Appl. No.: 18/451,238

(22) Filed: Aug. 17, 2023

(65) Prior Publication Data

US 2025/0061566 A1 Feb. 20, 2025

(51) Int. Cl.
| | |
|---|---|
| *G06T 7/00* | (2017.01) |
| *G06T 7/11* | (2017.01) |
| *G16H 10/60* | (2018.01) |
| *G16H 30/40* | (2018.01) |

(52) U.S. Cl.
CPC .............. *G06T 7/0012* (2013.01); *G06T 7/11* (2017.01); *G16H 10/60* (2018.01); *G16H 30/40* (2018.01); *G06T 2207/10072* (2013.01); *G06T 2207/20132* (2013.01); *G06T 2207/30064* (2013.01)

(58) Field of Classification Search
CPC . G06T 2207/30064; G06T 2207/20132; G06T 2207/10672; G06T 7/11; G06T 7/0012; G16H 30/40; G16H 10/60
See application file for complete search history.

(56) References Cited

U.S. PATENT DOCUMENTS

| | | |
|---|---|---|
| 2022/0061813 A1 | 3/2022 | Halmann et al. |
| 2024/0054700 A1* | 2/2024 | Truwit .................. G06T 11/006 |
| 2024/0087724 A1* | 3/2024 | Sawarkar ............... A61B 5/163 |

OTHER PUBLICATIONS

Li, Chengtai et al. "Natural Language Processing Applications for Computer-Aided Diagnosis in Oncology." Diagnostics (Basel) 13.2 (2023): 286. Web. (Year: 2023).*

Zhu, Wentao, et al. "Deepem: Deep 3d convnets with em for weakly supervised pulmonary nodule detection." Medical Image Computing and Computer Assisted Intervention—MICCAI 2018: 21st International Conference, Granada, Spain, Sep. 16-20, 2018, Proceedings, Part II 11. Springer International Publishing, 2018.

Yang, Hao-Hsiang, et al. "Leveraging auxiliary information from EMR for weakly supervised pulmonary nodule detection." Medical Image Computing and Computer Assisted Intervention—MICCAI 2021: 24th International Conference, Strasbourg, France, Sep. 27-Oct. 1, 2021, Proceedings, Part VII 24. Springer International Publishing, 2021.978-3-030-87234-2_24.

Sanchez, Rolando, et al. "Applying a Text-Search Algorithm to Radiology Reports Can Find More Patients With Pulmonary Nodules Than Radiology Coding Alone." Federal practitioner 37.Suppl 2 (2020): S32.

* cited by examiner

*Primary Examiner* — John R Wallace

(57) ABSTRACT

A framework for medical record-guided computer-aided detection. One or more properties of an object of interest previously reported in the one or more prior electronic medical records are extracted and used to crop a region of interest of a segmented body region in newly acquired medical image data of a patient. The object of interest may then be detected within the cropped region of interest.

20 Claims, 3 Drawing Sheets

300

100

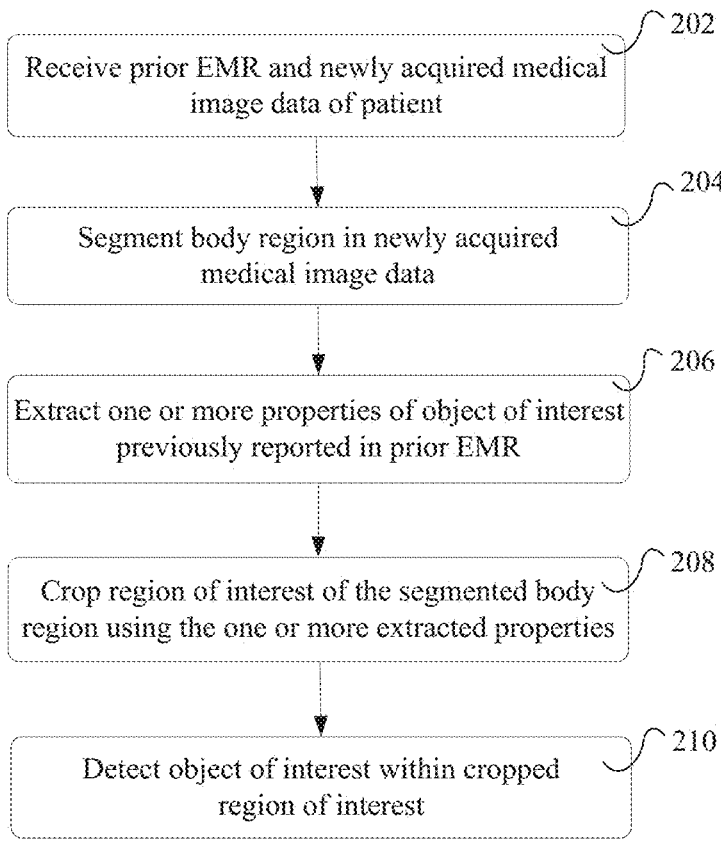

202

Receive prior EMR and newly acquired medical image data of patient

204

Segment body region in newly acquired medical image data

206

Extract one or more properties of object of interest previously reported in prior EMR

208

Crop region of interest of the segmented body region using the one or more extracted properties

210

Detect object of interest within cropped region of interest

MEDICAL RECORD-GUIDED COMPUTER-AIDED DETECTION

TECHNICAL FIELD

The present disclosure generally relates to data processing, and more particularly to a framework for medical record-guided computer-aided detection.

BACKGROUND

In clinical conditions, it is common for medical providers to have access to patients' prior electronic medical records. An electronic medical record (EMR) typically contains information of previously discovered nodules, pathological findings, with or without a detailed description of the corresponding properties (e.g., size, location in lung, density). During a lung cancer screening or a follow-up visit, radiologists need to visit previously detected nodules and check their development to decide the medical strategy.

As CT images have been used by radiologists to identify the occurrence of nodules, computer-aided diagnosis (CAD) algorithms have emerged to facilitate the reviewing process. For instance, a lung CAD system may serve as a secondary reader or concurrent first reader to assist radiologists with finding nodules in CT images. However, in both working modes, the CAD system needs to scan through the whole CT image volume and to complete the following steps: data preprocessing, lung segmentation, region proposal, post-classification and post-filtering. Most of these steps may involve deep learning neural networks.

The current CAD-assisted workflow requires the user to run the lung CAD system again on newly acquired CT images from the same patient. On average, it takes the lung CAD system around 3 to 4 minutes to process a standard chest CT series. During this time, the user must wait for the process to complete, which results in unnecessary delay in the reading workflow. In prior EMRs, nodules previously found are already described by texts, which usually include information such as locations in the CT image, nodule diameters, density and other characteristics of the nodules. It is a disadvantage to ignore such information provided in prior EMRs.

Another disadvantage of ignoring prior EMRs is that the findings provided by CAD may be inconsistent between newly acquired CT images and previously acquired CT images. The changes in CT acquisition parameters and body orientation during new CT scanning process may lead to inconsistent output findings compared to previous scans. If a nodule reported in the prior EMR is missing, the radiologist needs to manually refer to the reported location for an extra review. This is not only time-consuming, but also negatively impacts the radiologist's confidence in the CAD system.

SUMMARY

Described herein is a framework for computer-aided detection. One or more properties of an object of interest previously reported in the one or more prior electronic medical records are extracted and used to crop a region of interest (ROI) of a segmented body region in newly acquired medical image data of a patient. The object of interest may then be detected within the cropped region of interest.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

FIG. 2 shows an exemplary method of computer-aided detection; and

DETAILED DESCRIPTION

Figure 1:
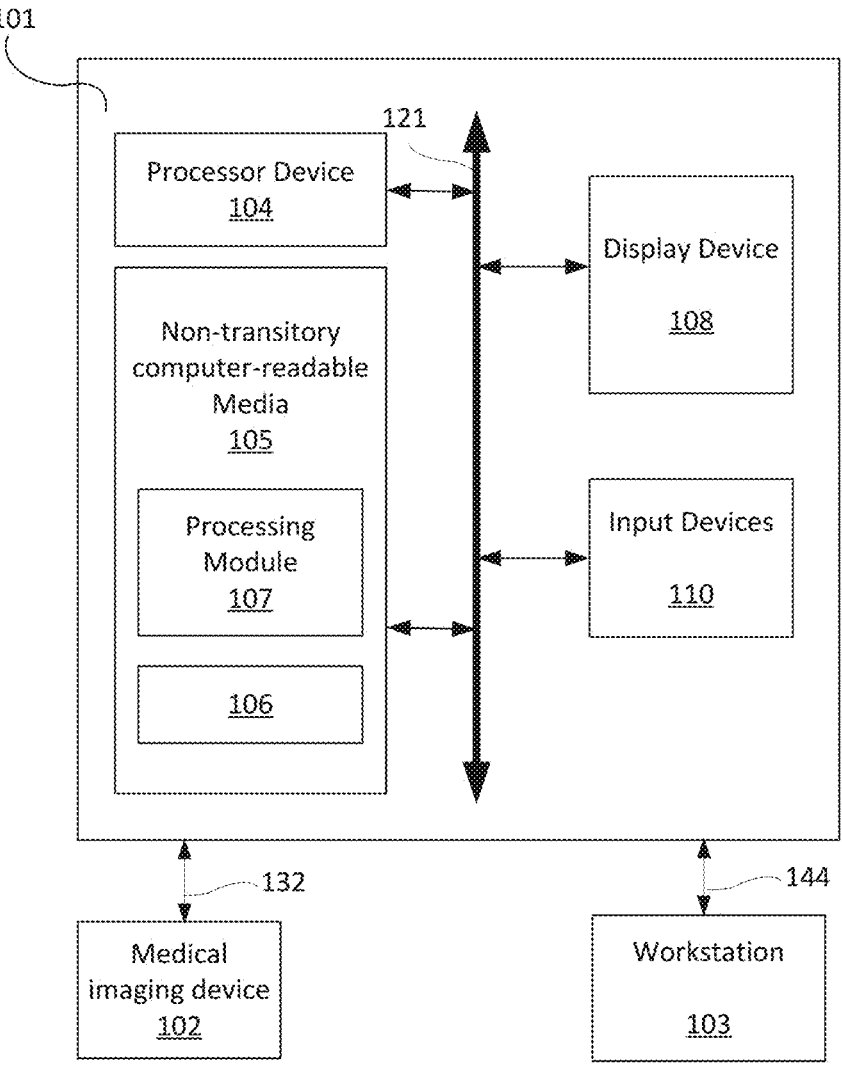
FIG. 1 shows a block diagram illustrating an exemplary system.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance. Independent of the grammatical term usage, individuals with male, female or other gender identities are included within the term."

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

For brevity, an image, or a portion thereof (e.g., a region of interest (ROI) in the image) corresponding to an object (e.g., a tissue, an organ, a tumor, etc., of a subject (e.g., a patient, etc.)) may be referred to as an image, or a portion of thereof (e.g., an ROI) of or including the object, or the object itself. For instance, an ROI corresponding to the image of a lung or a heart may be described as that the ROI includes a lung or a heart. As another example, an image of or including a chest may be referred to a chest image, or simply a chest. For brevity, that a portion of an image corresponding to an object is processed (e.g., extracted, segmented) may be described as the object is processed. For instance, that a portion of an image corresponding to a lung is extracted from the rest of the image may be described as that the lung is extracted.

In typical clinical workflows, radiologists either review newly acquired CT images from scratch if they are not assisted by computer-aided detection (CAD) algorithms, or wait for CAD system to complete detection process from scratch on the newly acquired CT images. It is time consuming to run CAD directly on the whole CT image series. Additionally, there is a chance that the CAD system may miss findings previously reported in the prior EMRs.

EMRs have been used to improve CAD algorithms for lung nodule detections. For example, the nodule information described in EMRs may be used to provide additional training labels or weakly supervised labels for nodule detections. These is evidence showing EMRs do contain information indicating nodule locations and nodule properties in CT images. Text extracted from medical reports can be useful for lung nodule detection.

A registration between prior CT image and current CT image may be performed to align the two CT images. However, this requires the knowledge of the world coordinates of findings in the prior CT image. In EMRs, however, radiologists do not report locations of findings in world coordinates. An alternative is to run CAD on the prior CT image. However, this is also very time-consuming and may miss the findings previously reported by readers in the prior EMR.

A framework for medical record-guided computer-aided detection is described herein. In accordance with one aspect, the framework facilitates a disease (e.g., lung cancer) follow-up reading workflow by utilizing information provided by prior EMRs. Radiologists may benefit from improved efficiency by being able to quickly locate nodules or other objects of interest described in the prior EMRs without waiting for software to scan the entire newly acquired CT image volume. The CAD algorithm may avoid missing findings that were previously reported in EMRs, even if the newly acquired CT images are significantly different from those acquired during the previous scans in terms of, for example, acquisition parameters.

Thus, the present framework increases efficiency by running local search instead of global search for objects of interest. By running object detection algorithm on a locally cropped ROI, significant amount of time is saved. Meanwhile, instead of performing a global general search for all types of nodules, specific finding as described in the report are detected, which is less likely to miss reported findings. The present framework may be designed to search for findings matching objects of interest described in the EMR, and the cropped ROI limits search range to improve the efficiency. These and other exemplary advantages and features will be described in more details in the following description.

FIG. 1 is a block diagram illustrating an exemplary system 100. The system 100 includes a computer system 101 for implementing the framework as described herein. In some implementations, computer system 101 operates as a standalone device. In other implementations, computer system 101 may be connected (e.g., using a network) to other machines, such as medical imaging device 102 and workstation 103. In a networked deployment, computer system 101 may operate in the capacity of a server (e.g., in a server-client user network environment, a client user machine in server-client user network environment, or as a peer machine in a peer-to-peer (or distributed) network environment).

In one implementation, computer system 101 includes a processor device or central processing unit (CPU) 104 coupled to one or more non-transitory computer-readable media 105 (e.g., computer storage or memory device), display device 108 (e.g., monitor) and various input devices 110 (e.g., mouse, touchpad or keyboard) via an input-output interface 121. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein are implemented as computer-readable program code tangibly embodied in one or more non-transitory computer-readable media 105. In particular, the present techniques may be implemented by a processing module 107. Non-transitory computer-readable media 105 may include random access memory (RAM), read-only memory (ROM), magnetic floppy disk, flash memory, and other types of memories, or a combination thereof. The computer-readable program code is executed by processor device 104 to process data provided by, for example, medical imaging device 102 and database 106. As such, the computer system 101 is a general-purpose computer system that becomes a specific-purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein. The same or different computer-readable media 105 may be used for storing a database 106, including, but not limited to, image datasets, a knowledge base, individual subject data, electronic medical records (EMRs), diagnostic reports (or documents) for subjects, or a combination thereof.

Medical imaging device 102 acquires medical image data 132. Such medical image data 132 may be processed by processing module 107. Medical imaging device 102 may be a radiology scanner and/or appropriate peripherals (e.g., keyboard and display device) for acquiring, collecting and/or storing such medical image data 132. Medical imaging device 102 may acquire medical image data 132 from a subject or patient by using techniques such as high-resolution computed tomography (HRCT), magnetic resonance (MR) imaging, computed tomography (CT), helical CT, X-ray, angiography, positron emission tomography (PET), fluoroscopy, ultrasound, single photon emission computed tomography (SPECT), or a combination thereof. Other types of imaging modalities are also useful.

Medical image data 132 is data that represents a medical image (or in certain examples more than one medical image). For example, medical image data 132 may comprise an array or list of pixel or voxel values. When processed by suitable image viewing software, the medical image data 132 results in a rendering of the medical image (or medical images) that it represents. The image file containing the medical image data 132 may further include one or more attributes and attribute values. The one or more attribute values are separate to and distinct from the medical image data 132, and instead comprise a text string indicating content of the medical image data 132. Such attribute values may, in some examples, be referred to as metadata of the image file. In some examples, the part of the image file that stores the attributes and attribute values may be referred to as a header of the image file, and the attributes and attribute values may be referred to as header data of the image file.

A specific example of an image file is a Digital Imaging and Communications in Medicine (DICOM) file. A DICOM file stores medical image data as pixel data in a designated data element, and further stores, as one or more other data elements, one or more attributes each having an attribute value comprising a text string indicating content of the medical image data. An example of such DICOM attribute is 'Study Description' whose attribute value is a text string that describes the study of which the medical imaging data is part (e.g., 'NERUO^HEAD' where the medical imaging data is of the head region of the patient) and thereby indicates the content of the medical imaging data. There are other examples of such DICOM attributes, such as 'Series description', 'Body Part Examined' as well as others.

Workstation 103 may include a computer and appropriate peripherals, such as a keyboard and display device, and can be operated in conjunction with the entire system 100. For example, workstation 103 may communicate with medical imaging device 102 so that the medical image data 132 can be presented or displayed at the workstation 103. The workstation 103 may communicate directly with the computer system 101 to display processed data and/or output results 144. The workstation 103 may include a graphical user interface to receive user input via an input device (e.g., keyboard, mouse, touch screen, voice or video recognition interface, etc.) to manipulate visualization and/or processing of the data.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

FIG. 2 shows an exemplary method 200 of computer-aided detection. It should be understood that the steps of the method 200 may be performed in the order shown or a different order. Additional, different, or fewer steps may also be provided. Further, the method 200 may be implemented with the system 100 of FIG. 1, a different system, or a combination thereof.

At 202, processing module 107 receives one or more prior electronic medical records (EMRs) and newly acquired medical image data of a patient. The one or more prior EMRs may be retrieved from, for example, database 106. The one or more prior EMRs contain information or findings entered during prior visits by the patient. The findings may describe physical and psychological occurrences of the patient surveyed by a healthcare provider during, for example, physical examinations by the healthcare provider's senses and/or medical devices (e.g., diagnostic or medical imaging device). The findings may describe one or more objects of interest, such as lung nodules, lesions or other abnormalities. The findings may indicate, for example, properties of such objects of interest (e.g., location, size, type, density). The newly acquired medical image data may be acquired by medical imaging device 102 during a current visit of the patient (i.e., after the one or more visits that generated the prior EMRs). For example, the newly acquired medical image data may be a CT image series acquired over various angles of the patient's body. Other types of medical image data may also be acquired.

At 204, processing module 107 segments a body region in the newly acquired medical image data to generate a segmented body region. In some implementations, the segmented body region includes different segments. For example, different lobes in a lung are segmented and recognized based on the newly acquired medical image data. In some implementations, the body region is segmented using attributes having attribute values that are stored in the image file (e.g., DICOM file) containing the newly acquired medical image data. See, for example, U.S. patent application Ser. No. 17/806,159, "Determining a Body Region represented by Medical Imaging Data," filed Jun. 9, 2022, which is herein incorporated by reference. One or more text strings associated with the attribute values may be input into a machine learning model that is trained to output a body region based on an input of one or more such text strings. Determining the body region based on the text strings of the image file may be less resource intensive and hence more efficient than, for example, determining the body region by extracting and analyzing the medical image data itself.

Alternatively, or in combination thereof, the body region is segmented by sampling voxels from the newly acquired medical image data around a single point of interest such that at least one voxel is skipped between two sampled voxels, and applying a trained classifier to the sampled voxels to identify the type of organ at the single point of interest. See, for example, U.S. patent application Ser. No. 18/312,822, "Method for identifying a type of organ in a volumetric medical image," filed May 5, 2023, which is herein incorporated by reference. The single point of interest is a point in the medical image data for which it is desired to identify the type of organ corresponding to said point. The single point of interest may be selected by a user At 206, processing module 107 extracts one or more properties of at least one object of interest previously reported in the prior EMRs. In some implementations, processing module 107 applies one or more natural language processing (NLP) techniques to recognize and extract properties (e.g., size, location, density) related to the object of interest (e.g., lung nodule) previously reported in prior EMRs. The properties extracted from the prior EMRs may include, but are not limited to, location, density, size or diameter of the object of interest. Other properties may also be extracted. The location of the object of interest may be described with reference to the segmented body section without the use of coordinates. For example, the EMR may include the following description of the location of a lung nodule in plain language: "lateral segment of the middle lobe of the right lung."

The NLP techniques used to extract the properties of the object of interest include, for example, artificial intelligence or machine learning techniques (e.g., deep neural networks). In some implementations, the properties are extracted from a patient data model (PDM) that is generated from the prior EMRs. A PDM is an abstract model that organizes elements of patient data and standardizes how they relate to one another and to properties of real-world entities. A PDM is the central base upon which various clinical workflows store and exchange data. All data should be described according to the common PDM (cPDM) to be exchanged across different systems. A PDM makes the data searchable. For example, "the patient's lung nodule locations" may be extracted by querying using Systematized Nomenclature of Medicine (SNOMED) codes (e.g., 786838002 for lung nodule and 246267002 for location) as the search keys.

The PDM may be generated using artificial intelligence (AI) techniques. In some implementations, an AI engine decomposes each description in an EMR to WHAT (i.e., abnormality or disease/pathology findings) and WHERE (i.e., anatomical location of abnormality. The AI engine may include a neural parser and a named entity recognition module to perform such decomposition. The results may be formatted in accordance with the Fast Healthcare Interoperability Resources (FHIR) standard. Other formats are also useful. The AI engine may assign SNOMED codes to the search keys, thereby allowing the PDM to be searchable using SNOMED codes. Besides the SNOMED code search, semantic search for similar phrases and sentences without the need for string match using AI may also be enabled. Alternatively, the PDM may also searched via Question and Answering by asking a question written in a natural language for the system.

At 208, processing module 107 crops a region of interest of the segmented body region using the one or more extracted properties of the object of interest. For example, a region of interest (ROI) containing the object of interest is cropped at the extracted location within the segmented body region. The region of interest may contain at least one entire segment of the segmented body region. The region of interest may be defined by a rectangle, a square, or any other geometric shape.

At 210, processing module 107 detects the at least one object of interest within the cropped region of interest. An object detection algorithm may be used to quickly process the small region of interest. Exemplary object detection algorithms include, but are not limited to, neural-based or machine learning techniques, as well as non-neural based techniques. The detected object of interest matching the description in the prior EMR may be shown to the user via, for example, workstation 103. For example, a non-cancerous solid nodule in a left lower lung of size 5 mm was described in the EMR. Processing module 107 may detect the nodule within the cropped region of interest and display it to the user.

Processing module 107 may highlight the detected object of interest in the cropped region of interest. In some implementations, processing module 107 may highlight the detected object of interest by displaying a text label (e.g., "type: solid, size: 5 mm, malignant: No") describing the nodule. For example, the text label may be displayed next to the nodule when the user selects the nodule on the medical image via a user interface. In some implementations, the nodule and/or its label are highlighted with relevant text in the prior EMR. For example, the nodule and/or its label are displayed in the same color as the relevant text, while irrelevant text is displayed in a different color. Other types of highlighting, such as using the same font or shading, may also be applied.

Figure 3:
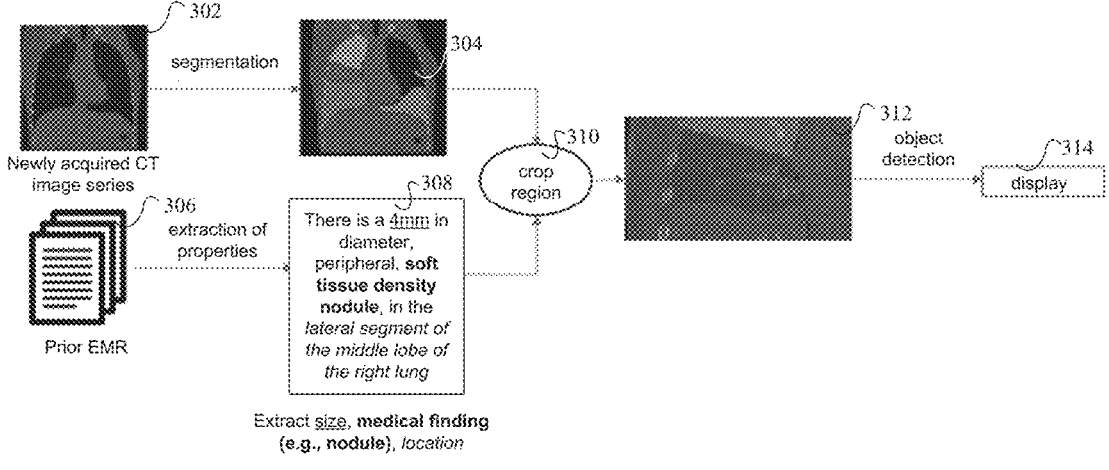
FIG. 3 shows an exemplary method of computer-aided detection of lung nodules.

FIG. 3 shows an exemplary method 300 of computer-aided detection of lung nodules in accordance with one implementation. It should be understood that the steps of the method 300 may be performed in the order shown or a different order. Additional, different, or fewer steps may also be provided. Further, the method 300 may be implemented with the system 100 of FIG. 1, a different system, or a combination thereof.

Processing module 107 receives a newly acquired chest CT image series 302 of a patient and one or more prior electronic medical records 306. Processing module 107 segments a lung region in the newly acquired medical image data 302 into different lung lobe segments 304. Segmentation may be performed using, for example, a single point of interest selected by a user. Other types of segmentation algorithms are also useful.

Processing module 107 further extracts properties of a lung nodule previously reported in the prior EMRs 306. In some implementations, processing module 107 applies natural language processing (NLP) techniques to recognize and extract the medical finding, size and location related to lung nodules previously reported in at least one section 308 of a prior EMR 306.

At 310, processing module 107 crops a region of interest 312 of the segmented lung region 304 using the extracted location of the lung nodule. The region of interest may be defined by a rectangle that contains at least one entire lung lobe region. Processing module 107 may then detect the lung nodule within the cropped region of interest 312.

At 314, the detected nodule is highlighted and displayed to the user.

The following is a list of non-limiting illustrative embodiments disclosed herein:

Illustrative embodiment 1. A data processing system, comprising: a non-transitory memory device for storing computer readable program code; and a processor device in communication with the non-transitory memory device, the processor device being operative with the computer readable program code to perform steps including: receiving one or more prior electronic medical records and newly acquired medical image data of a patient, segmenting a body region in the newly acquired medical image data to generate a segmented body region, extracting one or more properties of an object of interest previously reported in the one or more prior electronic medical records, cropping a region of interest of the segmented body region using the one or more properties to generate a cropped region of interest, detecting the object of interest within the cropped region of interest, and highlighting the object of interest in the cropped region of interest.

Illustrative embodiment 2. The data processing system of illustrative embodiment 1 wherein the newly acquired medical image data comprises medical image data acquired by high-resolution computed tomography (HRCT), magnetic resonance (MR) imaging, computed tomography (CT), helical CT, X-ray, angiography, positron emission tomography (PET), fluoroscopy, ultrasound, single photon emission computed tomography (SPECT), or a combination thereof.

Illustrative embodiment 3. The data processing system of illustrative embodiments 1-2 wherein segmenting the body region comprises segmenting different lobes in a lung.

Illustrative embodiment 4. The data processing system of illustrative embodiments 1-3 wherein segmenting the body region comprises determining the segmented body region using attributes stored in an image file containing the newly acquired medical image data.

Illustrative embodiment 5. The data processing system of illustrative embodiments 1-4 wherein the one or more properties comprise a location of the object of interest.

Illustrative embodiment 6. The data processing system of illustrative embodiments 1-5 wherein the one or more properties comprise a size, diameter or density of the object of interest.

Illustrative embodiment 7. The data processing system of illustrative embodiments 1-6 wherein extracting the one or more properties of the object of interest previously reported in the one or more prior electronic medical records comprises applying one or more natural language processing techniques.

Illustrative embodiment 8. The data processing system of illustrative embodiments 1-7 wherein highlighting the object of interest in the cropped region of interest comprises displaying a text label describing the object of interest.

Illustrative embodiment 9. A method, comprising: receiving one or more prior electronic medical records and newly acquired medical image data of a patient; segmenting a body region in the newly acquired medical image data to generate a segmented body region; extracting one or more properties of an object of interest previously reported in the one or more prior electronic medical records; cropping a region of interest of the segmented body region using the one or more properties to generate a cropped region of interest; and detecting the object of interest within the cropped region of interest.

Illustrative embodiment 10. The method of illustrative embodiment 9 wherein segmenting the body region comprises segmenting different lobes in a lung.

Illustrative embodiment 11. The method of illustrative embodiments 9-10 wherein the object of interest comprises a lung nodule.

Illustrative embodiment 12. The method of illustrative embodiments 9-11 wherein the one or more properties comprise a location of the object of interest.

Illustrative embodiment 13. The method of illustrative embodiment 9-12 wherein the one or more properties comprise a size, diameter or density of the object of interest.

Illustrative embodiment 14. The method of illustrative embodiments 9-13 wherein extracting one or more properties of the object of interest previously reported in the one or more prior electronic medical records comprises applying one or more natural language processing techniques.

Illustrative embodiment 15. The method of illustrative embodiments 9-14 further comprises highlighting the object of interest in the cropped region of interest.

Illustrative embodiment 16. The method of illustrative embodiment 15 wherein highlighting the object of interest in the cropped region of interest comprises displaying a text label describing the object of interest.

Illustrative embodiment 17. The method of illustrative embodiment 16 wherein highlighting the object of interest in the cropped region of interest further comprises highlighting the text label and relevant text in the prior electronic medical records using a same color.

Illustrative embodiment 18. One or more non-transitory computer readable media embodying a program of instructions executable by machine to perform steps comprising: segmenting a body region in newly acquired medical image data to generate a segmented body region; extracting one or more properties of an object of interest previously reported in one or more prior electronic medical records; cropping a region of interest of the segmented body region using the one or more properties to generate a cropped region of interest; and detecting the object of interest within the cropped region of interest.

Illustrative embodiment 19. The one or more non-transitory computer readable media of illustrative embodiment 18 wherein the steps further comprise highlighting the object of interest in the cropped region of interest.

Illustrative embodiment 20. The one or more non-transitory computer readable media of illustrative embodiment 19 wherein highlighting the object of interest in the cropped region of interest comprises displaying a text label describing the object of interest.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A data processing system, comprising:
a non-transitory memory device for storing computer readable program code; and
a processor device in communication with the non-transitory memory device, the processor device being operative with the computer readable program code to perform steps including
receiving one or more prior electronic medical records and newly acquired medical image data of a patient,
segmenting a body region in the newly acquired medical image data to generate a segmented body region,
extracting one or more properties of an object of interest previously reported in text of the one or more prior electronic medical records,
cropping a region of interest of the segmented body region using the one or more properties to generate a cropped region of interest,
detecting the object of interest within the cropped region of interest, and
highlighting the object of interest in the cropped region of interest and relevant text in the one or more prior electronic medical records.

2. The data processing system of claim 1 wherein the newly acquired medical image data comprises medical image data acquired by high-resolution computed tomography (HRCT), magnetic resonance (MR) imaging, computed tomography (CT), helical CT, X-ray, angiography, positron emission tomography (PET), fluoroscopy, ultrasound, single photon emission computed tomography (SPECT), or a combination thereof.

3. The data processing system of claim 1 wherein segmenting the body region comprises segmenting different lobes in a lung.

4. The data processing system of claim 1 wherein segmenting the body region comprises determining the segmented body region using attributes stored in an image file containing the newly acquired medical image data.

5. The data processing system of claim 1 wherein the one or more properties comprise a location of the object of interest.

6. The data processing system of claim 1 wherein the one or more properties comprise a size, diameter or density of the object of interest.

7. The data processing system of claim 1 wherein extracting the one or more properties of the object of interest previously reported in the text of the one or more prior electronic medical records comprises applying one or more natural language processing techniques.

8. The data processing system of claim 1 wherein highlighting the object of interest in the cropped region of interest comprises displaying a text label describing the object of interest.

9. A method, comprising:

receiving one or more prior electronic medical records and newly acquired medical image data of a patient;

segmenting a body region in the newly acquired medical image data to generate a segmented body region;

extracting one or more properties of an object of interest previously reported in text of the one or more prior electronic medical records;

cropping a region of interest of the segmented body region using the one or more properties to generate a cropped region of interest;

detecting the object of interest within the cropped region of interest; and highlighting the object of interest in the cropped region of interest and relevant text in the one or more prior electronic medical records.

10. The method of claim 9 wherein segmenting the body region comprises segmenting different lobes in a lung.

11. The method of claim 9 wherein the object of interest comprises a lung nodule.

12. The method of claim 9 wherein the one or more properties comprise a location of the object of interest.

13. The method of claim 9 wherein the one or more properties comprise a size, diameter or density of the object of interest.

14. The method of claim 9 wherein extracting the one or more properties of the object of interest previously reported in the text of the one or more prior electronic medical records comprises applying one or more natural language processing techniques.

15. The method of claim 9 wherein highlighting the object of interest in the cropped region of interest and the relevant text in the one or more prior electronic medical records comprises highlighting the object of interest and the relevant text in the one or more prior electronic medical records using a same color.

16. The method of claim 9 wherein highlighting the object of interest in the cropped region of interest comprises displaying a text label describing the object of interest.

17. The method of claim 16 wherein highlighting the object of interest in the cropped region of interest and the relevant text in the one or more prior electronic medical records comprises highlighting the text label and the relevant text in the one or more prior electronic medical records using a same color.

18. One or more non-transitory computer readable media embodying a program of instructions executable by machine to perform steps comprising:

segmenting a body region in newly acquired medical image data to generate a segmented body region;

extracting one or more properties of an object of interest previously reported in text of one or more prior electronic medical records;

cropping a region of interest of the segmented body region using the one or more properties to generate a cropped region of interest; and detecting the object of interest within the cropped region of interest; and highlighting the object of interest in the cropped region of interest and relevant text in the one or more prior electronic medical records.

19. The one or more non-transitory computer readable media of claim 18 wherein highlighting the object of interest in the cropped region of interest and the relevant text in the one or more prior electronic medical records comprises highlighting the object of interest and the relevant text in the one or more prior electronic medical records using a same color.

20. The one or more non-transitory computer readable media of claim 18 wherein highlighting the object of interest in the cropped region of interest comprises displaying a text label describing the object of interest.

\* \* \* \* \*